United States Patent
Bates et al.

(10) Patent No.: US 10,155,102 B2
(45) Date of Patent: Dec. 18, 2018

(54) SYSTEM AND METHOD FOR EXTERNAL PERCUTANEOUS CONNECTIONS

(71) Applicant: Cook Medical Technologies LLC, Bloomington, IN (US)

(72) Inventors: Gregory Bates, Advance, NC (US); Hilbert Brown, Winston-Salem, NC (US); Casandra Niebel, Winston-Salem, NC (US); Smitha Raghunathan, Winston-Salem, NC (US); Maximiliano Soetermans, Pinnacle, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 566 days.

(21) Appl. No.: 14/453,052

(22) Filed: Aug. 6, 2014

(65) Prior Publication Data

US 2015/0045615 A1 Feb. 12, 2015

Related U.S. Application Data

(60) Provisional application No. 61/862,747, filed on Aug. 6, 2013.

(51) Int. Cl.
*A61B 1/00* (2006.01)
*A61M 39/02* (2006.01)
(Continued)

(52) U.S. Cl.
CPC ..... *A61M 39/0247* (2013.01); *A61B 17/3415* (2013.01); *A61J 15/0015* (2013.01);
(Continued)

(58) Field of Classification Search
CPC . A61B 17/34; A61B 17/3415; A61B 17/3417; A61B 2017/3419;
(Continued)

(56) References Cited

U.S. PATENT DOCUMENTS 5,895,404 A  4/1999 Ruiz
7,041,050 B1 * 5/2006 Ronald .......... A61B 17/320016
                                                    600/104
(Continued)

FOREIGN PATENT DOCUMENTS

CN      102068292 A    5/2011
WO  2002/019890 A2    3/2002
(Continued)

OTHER PUBLICATIONS

European Patent Office, International Search Report of International Application No. PCT/US2014/049915, dated Feb. 2, 2015, 6 pages.

*Primary Examiner* — Alexandra L Newton
(74) *Attorney, Agent, or Firm* — Brinks Gilson & Lione

(57) ABSTRACT

The present invention provides a system and method for creating a percutaneous fluidic connection. In one embodiment, the system includes an endoscope having an end cap with a tube that defines a distal cavity and an internal magnet circumferentially arranged around the distal end of the tube. The internal magnet is delivered into the patient's stomach and pressed against an inner wall of the stomach. An external magnet is placed on an external surface of the patient's skin corresponding to the location of the internal magnet and the inner and external magnets are coupled together. An incision is made through the skin to access the distal cavity, and an overtube containing a PEG device is inserted into the distal cavity. The magnets are decoupled and removed, leaving the overtube in place, which is subsequently retracted from the PEG device, allowing the PEG device to be anchored in place.

7 Claims, 11 Drawing Sheets

(51) Int. Cl.
*A61B 17/34* (2006.01)
*A61J 15/00* (2006.01)
*A61B 17/00* (2006.01)

(52) U.S. Cl.
CPC ....... *A61B 1/00089* (2013.01); *A61B 1/00101* (2013.01); *A61B 1/00137* (2013.01); *A61B 2017/00876* (2013.01); *A61M 2039/027* (2013.01); *A61M 2039/0291* (2013.01)

(58) Field of Classification Search
CPC ............ A61B 17/3421; A61B 17/3423; A61B 17/32053; A61B 2017/347; A61B 2017/348; A61B 17/3494; A61B 17/3496; A61B 1/00137; A61B 1/00089; A61B 1/00101; A61B 1/0014; A61M 2039/0261; A61M 39/0247; A61M 2039/027; A61M 25/02; A61M 2025/0233; A61M 2039/0255
See application file for complete search history.

(56) References Cited

U.S. PATENT DOCUMENTS

| | | | |
|---|---|---|---|
| 2002/0128602 | A1* | 9/2002 | Adams ............. A61B 17/00234 604/164.1 |
| 2007/0173878 | A1 | 7/2007 | Heuser |
| 2008/0114384 | A1 | 5/2008 | Chang et al. |
| 2010/0010311 | A1* | 1/2010 | Miller ................. A61B 1/0008 600/156 |
| 2011/0288534 | A1 | 11/2011 | Aguirre et al. |
| 2012/0010571 | A1 | 1/2012 | Adams et al. |

FOREIGN PATENT DOCUMENTS

| | | |
|---|---|---|
| WO | 2003/097124 A2 | 11/2003 |
| WO | 2005/048814 A2 | 6/2005 |

* cited by examiner

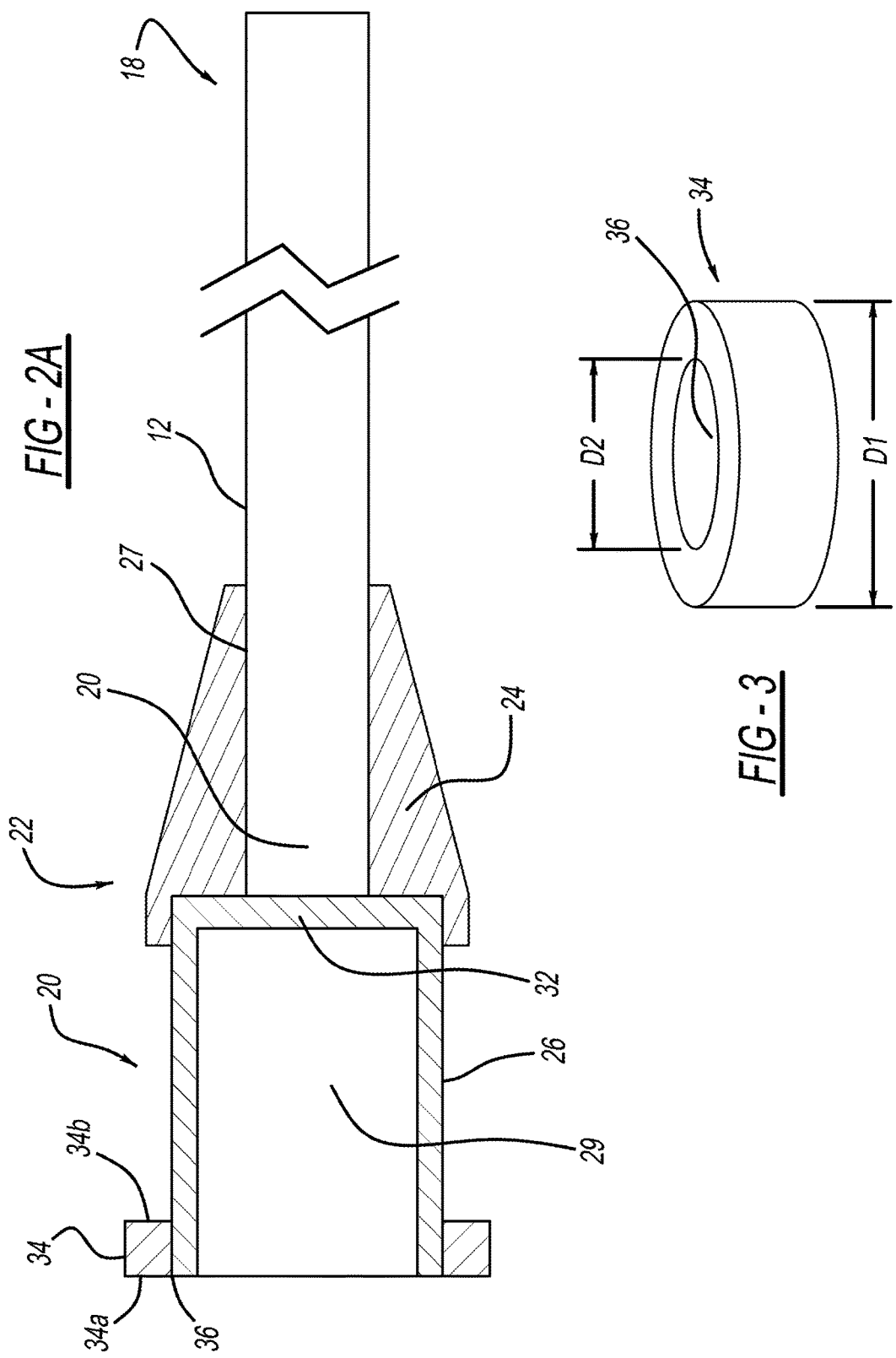

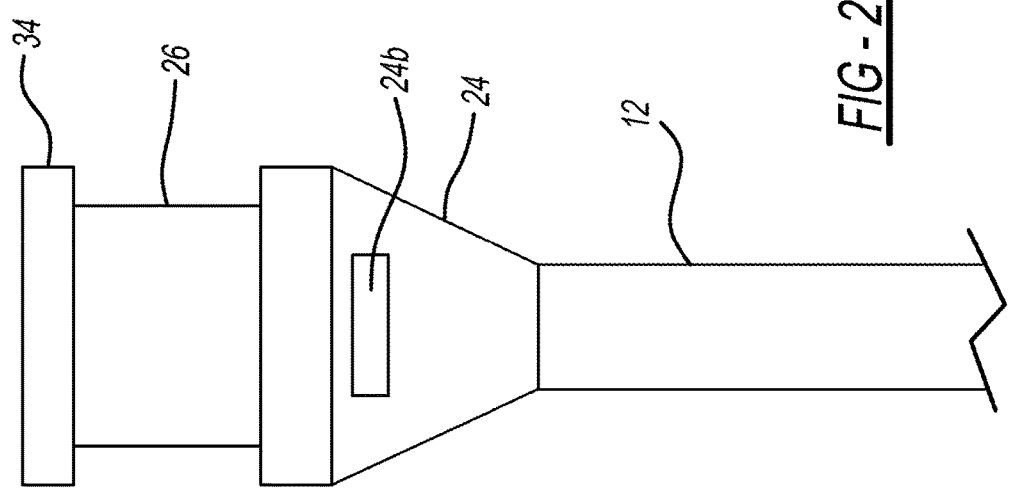
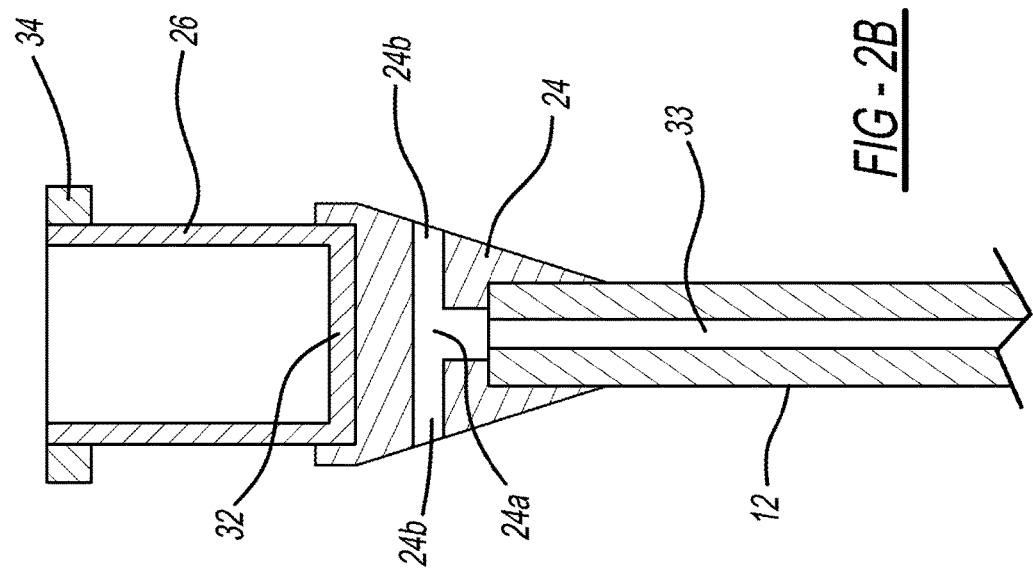

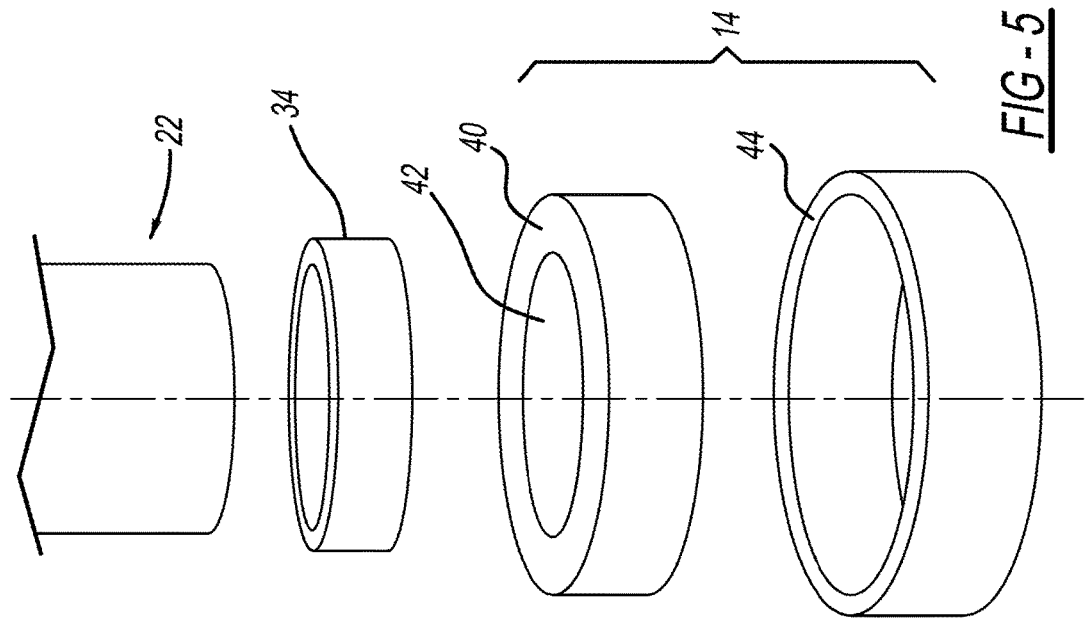
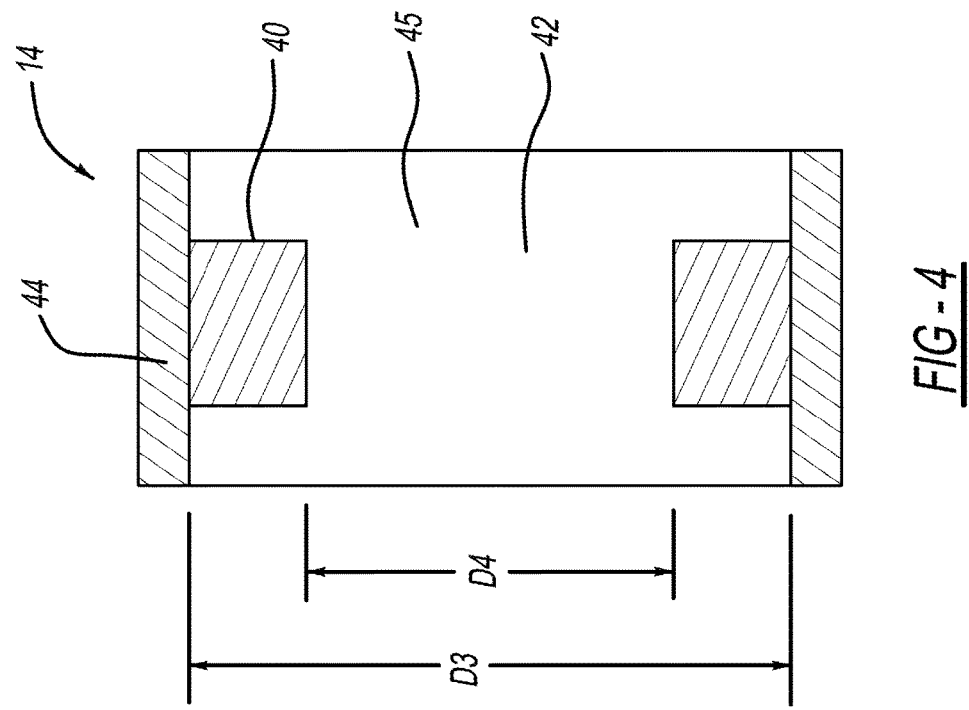

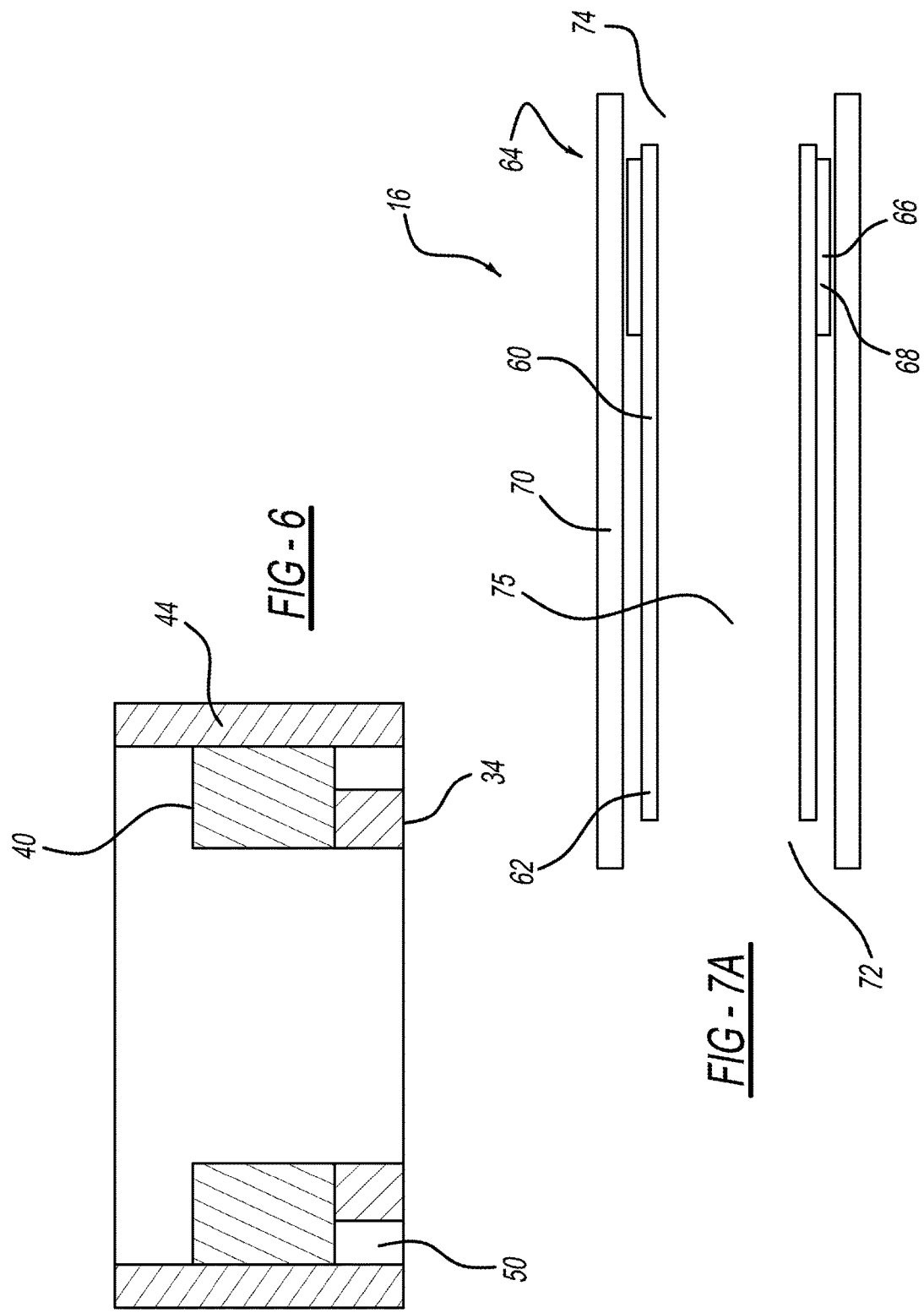

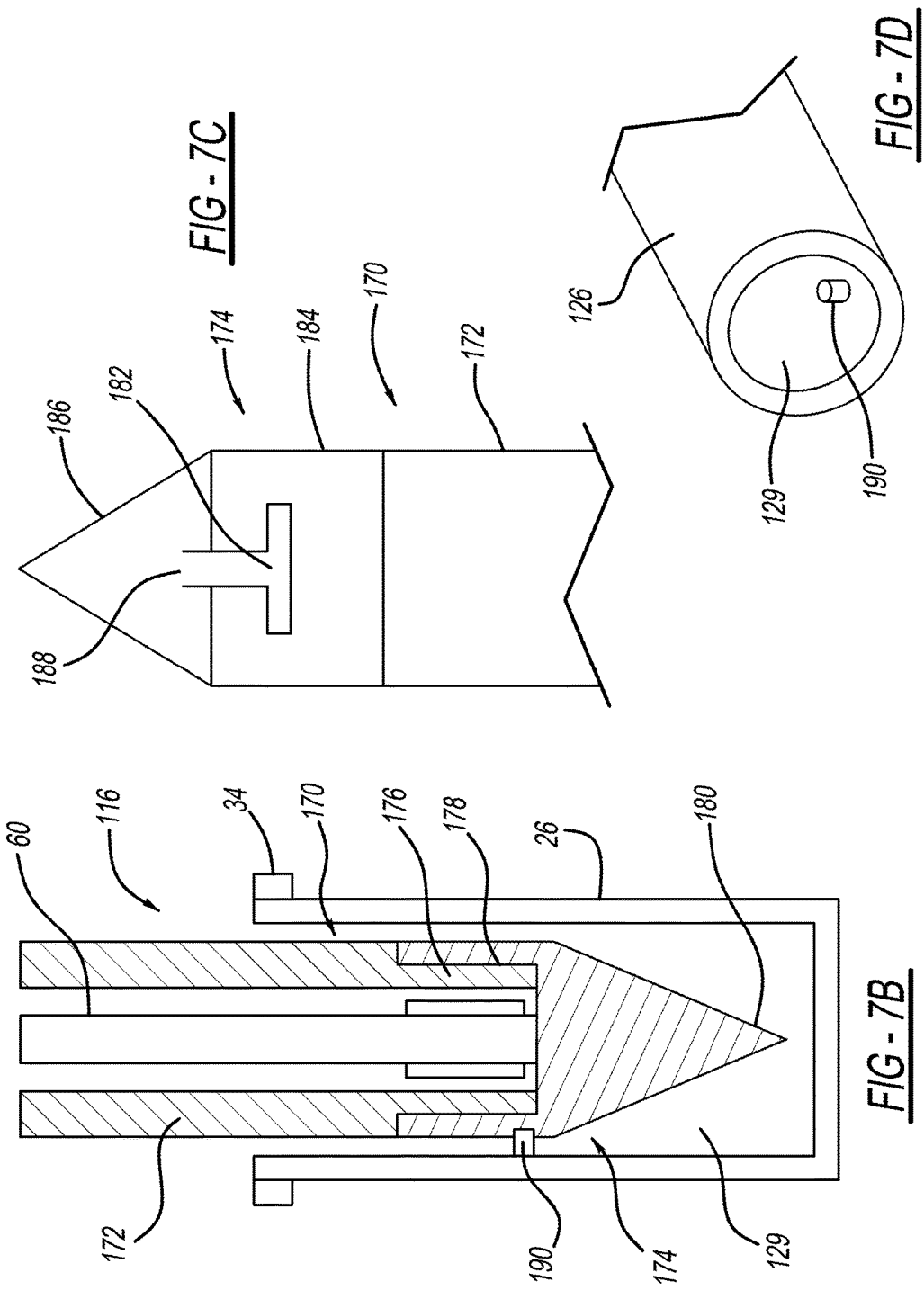

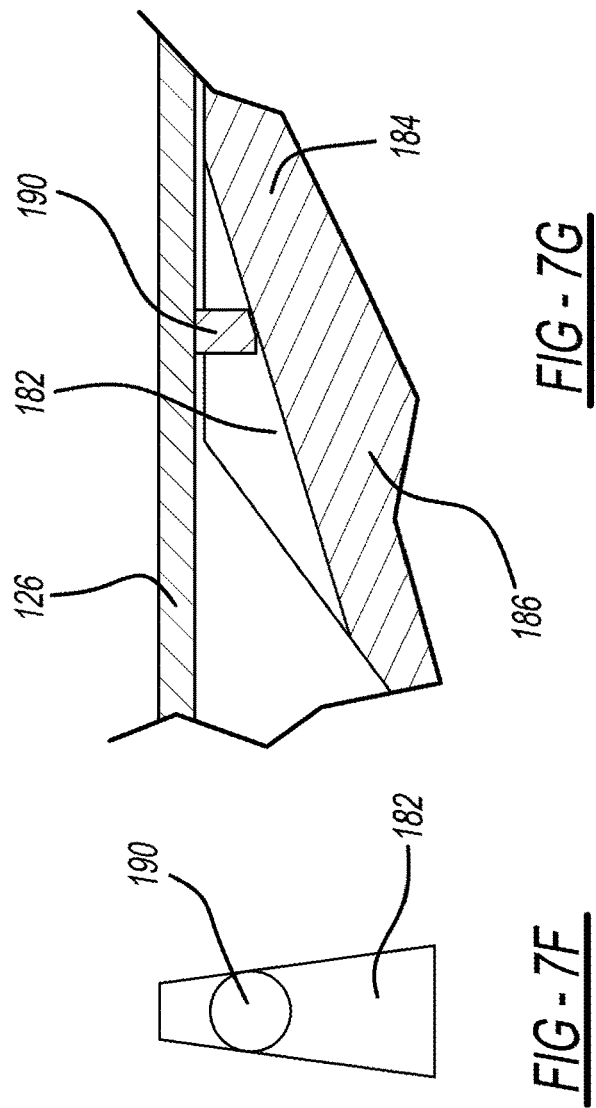
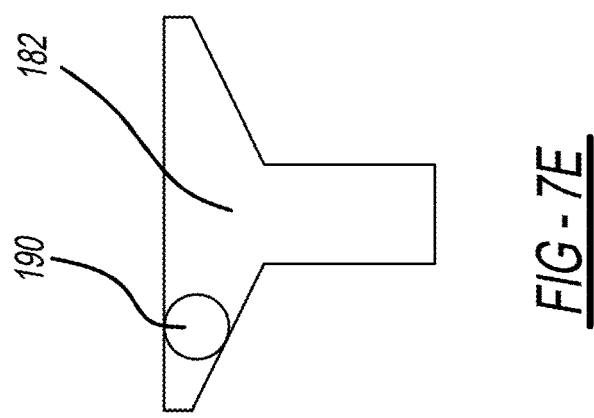
FIG-7G
FIG-7F
FIG-7E

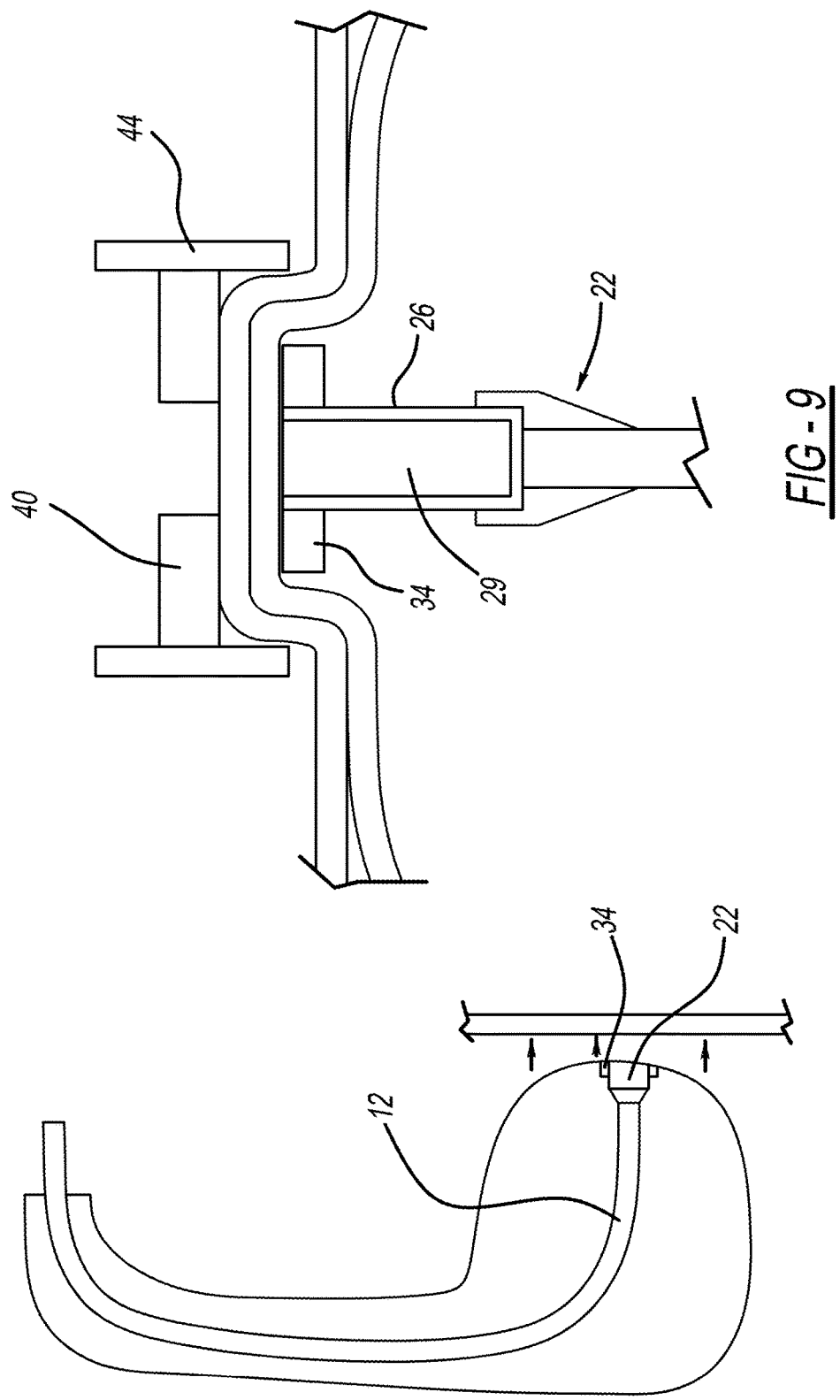

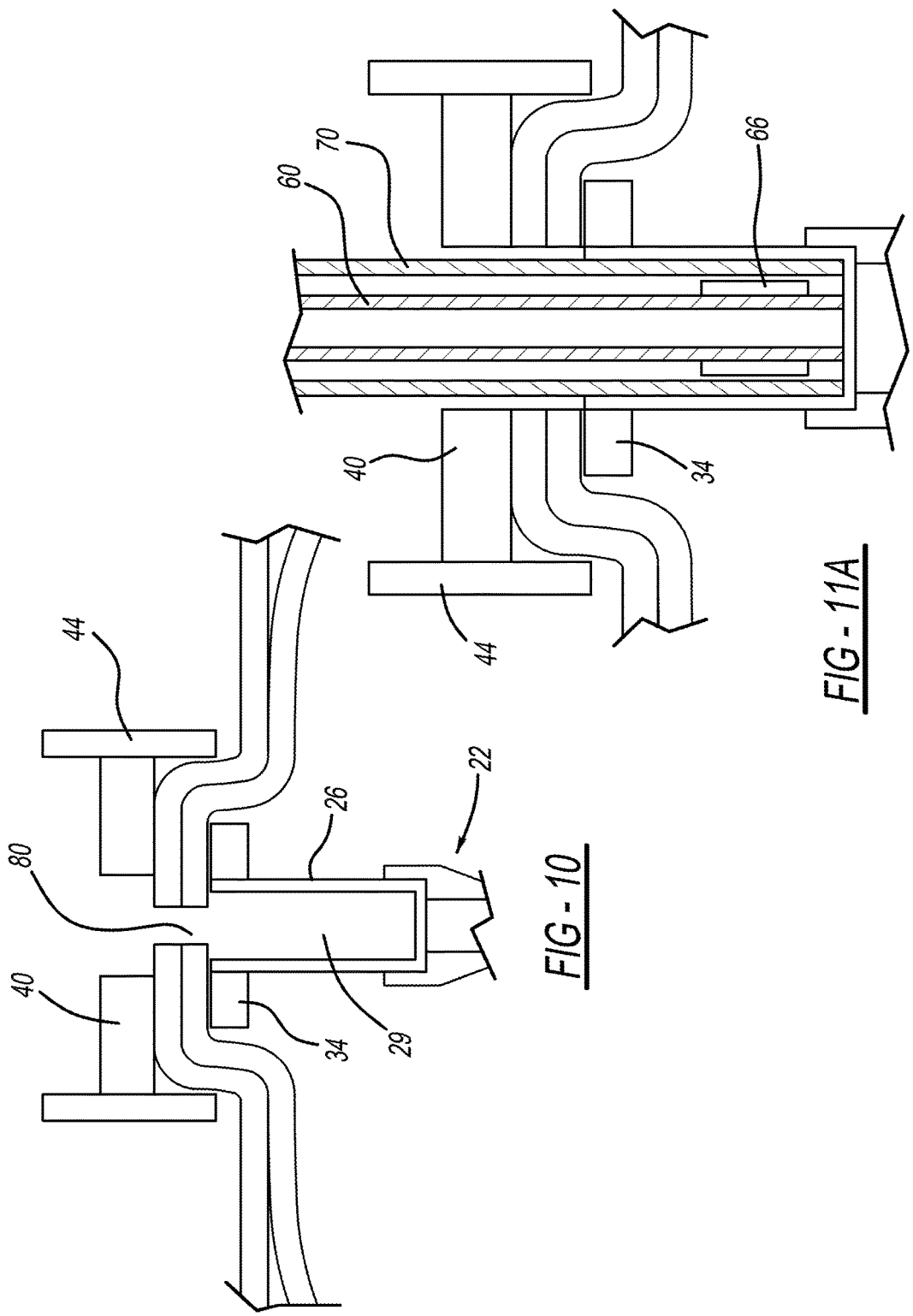

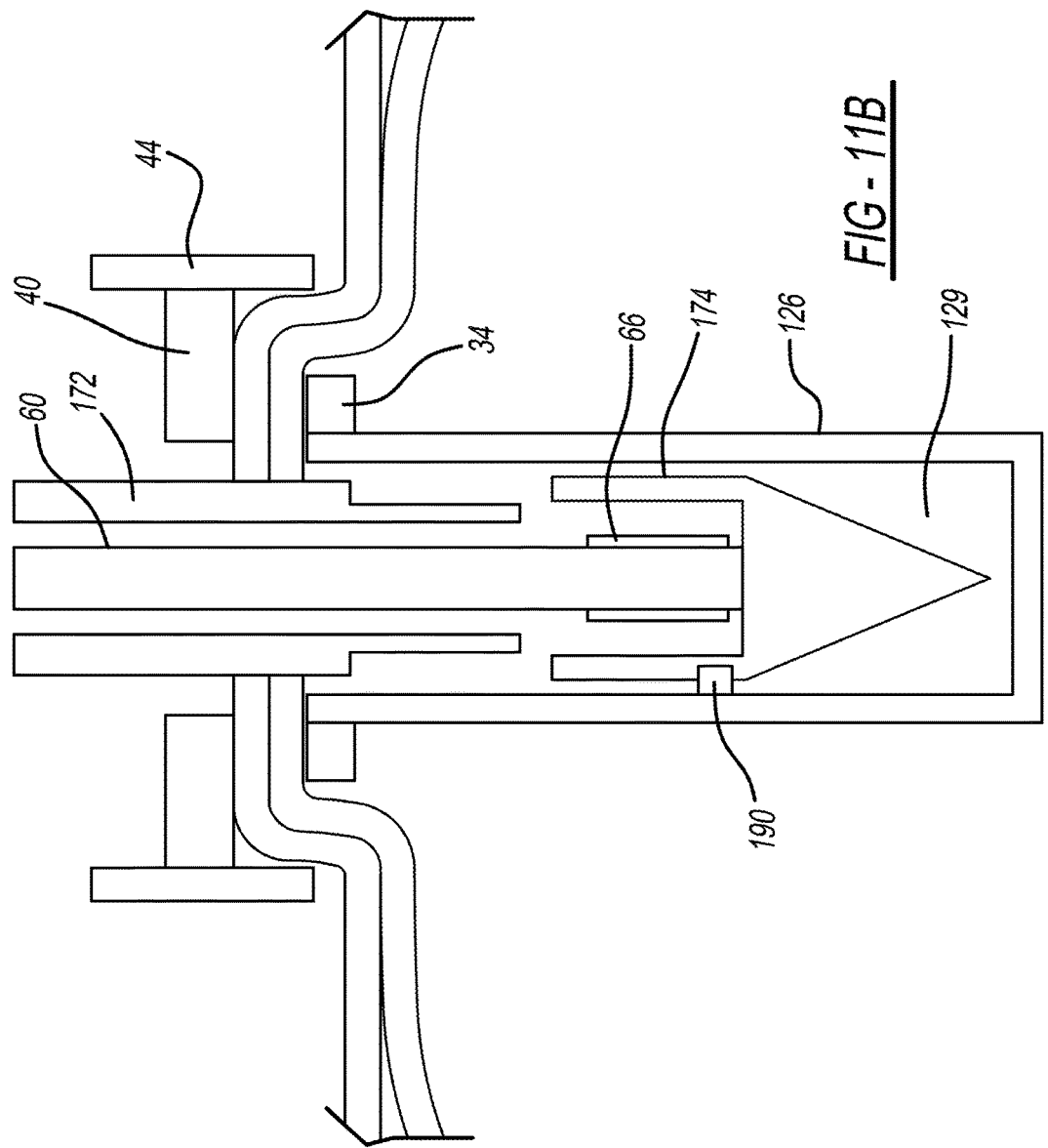

SYSTEM AND METHOD FOR EXTERNAL PERCUTANEOUS CONNECTIONS

CROSS REFERENCE TO RELATED APPLICATIONS

This application claims the benefit of U.S. Provisional Application No. 61/862,747, filed Aug. 6, 2013, the contents of which is incorporated by reference in its entirety herein.

FIELD OF THE INVENTION

The present invention relates generally to external percutaneous connections to an internal organ or bodily lumen.

BACKGROUND OF THE INVENTION

Many types of external percutaneous connections form to provide a patient or medical staff with access to an internal organ or bodily lumen. For example, semi-permanent connections are made through the skin for placement of IV lines, catheters, dialysis lines, colostomy bags in the like. Percutaneous endoscopic gastrostomy tubes, commonly known as PEG tubes, are used as a means of feeding when a person is unable to eat. PEG tubes are typically inserted through a small incision in the abdomen into the stomach. These tubes may be form placed, or large support bolsters having adhesive pad are used to anchor the tube in place such that a portion extends into the stomach, and an opposing portion extends out of the stomach and through the skin for external access.

BRIEF SUMMARY OF THE INVENTION

The present invention provides a system and method for creating an external percutaneous fluidic connection. In one embodiment, a medical system for creating a percutaneous external connection with a tubular medical device is provided, the medical system comprising: an elongate endoscope for being inserted into a patient's body cavity; an end cap attached to a distal end of the endoscope, the end cap including a barrel and a tube, the tube defining a cavity having a distal opening; an internal magnet attached to a distal end of the tube, the internal magnet being circumferentially arranged around the distal end of the tube, wherein the tube extends at least partially into an aperture defined by the internal magnet; and an external magnet configured for mating with the internal magnet, wherein the external magnet defines an aperture, wherein the external magnet is attracted to the internal magnet; wherein the apertures of the external magnet and the internal magnet are sized to permit passage of the tubular medical device therethrough and the cavity of the tube is sized to receive the tubular medical device therein.

In another embodiment, a method for creating a percutaneous fluidic connection is provided, the method comprising: inserting an elongate endoscope into an orifice of a patient, wherein the endoscope includes an end cap having a tube disposed at the distal end thereof, the tube defining a distal cavity, and a first annular magnet is disposed at the distal end of the tube; advancing the distal end of the endoscope through a body passage and toward a body cavity; advancing the endoscope and the first annular magnet against an inner surface of a wall of the body cavity; placing a second annular magnet on an outer surface of the patient's skin at a location corresponding to the location of the first annular magnet, wherein the first and second annular magnets are aligned; magnetically coupling the first and second annular magnets; creating an incision through the patient's skin and the body cavity wall with a cutting tool to create fluid communication between the distal cavity of the tube and the exterior of the patient's body; inserting a tubular medical device through the incision and the first and second annular magnets and into the distal cavity of the tube; decoupling the first and second annular magnets; retracting the endoscope from the patient's body; and anchoring the tubular medical device.

BRIEF DESCRIPTION OF THE DRAWINGS

FIG. 2A is a schematic cross-sectional view showing the endoscope, end cap, and internal magnet;

FIG. 2B is a schematic cross-sectional viewing showing an end cap having a channel and openings in the side;

FIG. 2C is a front view of the end cap of FIG. 2B showing the openings;

FIG. 3 is an isometric view of the internal magnet;

FIG. 4 is a cross-sectional view showing the external ring having the external magnet and jacket;

FIG. 5 is an exploded view showing a tube of the end cap, the internal magnet, the external magnet, and the jacket;

FIG. 6 is a cross-sectional view showing the internal magnet received within the jacket and mated with the external magnet without material sandwiched between the magnets;

FIG. 7A is a schematic cross-sectional view showing the tubular medical device housed within the overtube;

FIG. 7B is a schematic cross-sectional view showing an alternative overtube having a tapered portion at the end, with the overtube and tapered portion received within a cavity of the end cap;

FIG. 7C is a front view of the overtube of FIG. 7B showing a locking channel formed in the side of the overtube;

FIG. 7D is a isometric view showing a peg extending into the cavity of the end cap;

FIG. 7E is a schematic view of an alternative locking channel with the peg received therein;

FIG. 7F is a schematic view of another alternative locking channel with the peg received therein;

FIG. 7G is a schematic cross-sectional view of another alternative locking channel with the peg received therein;

FIG. 8 is a schematic view showing the endoscope inserted through an orifice into a body cavity of a patient;

FIG. 9 is a schematic view showing the inner and external magnets being coupled with the patient's skin and inner wall of the body cavity sandwiched between the magnets;

FIG. 10 is a schematic view showing an incision through the patient's skin and body cavity wall;

FIG. 11A is a schematic view showing the overtube having the tubular medical device inserted through the incision and into a distal cavity of the end cap;

FIG. 11B is a schematic view showing the alternative overtube in a de-coupled configuration within the cavity of the end cap;

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
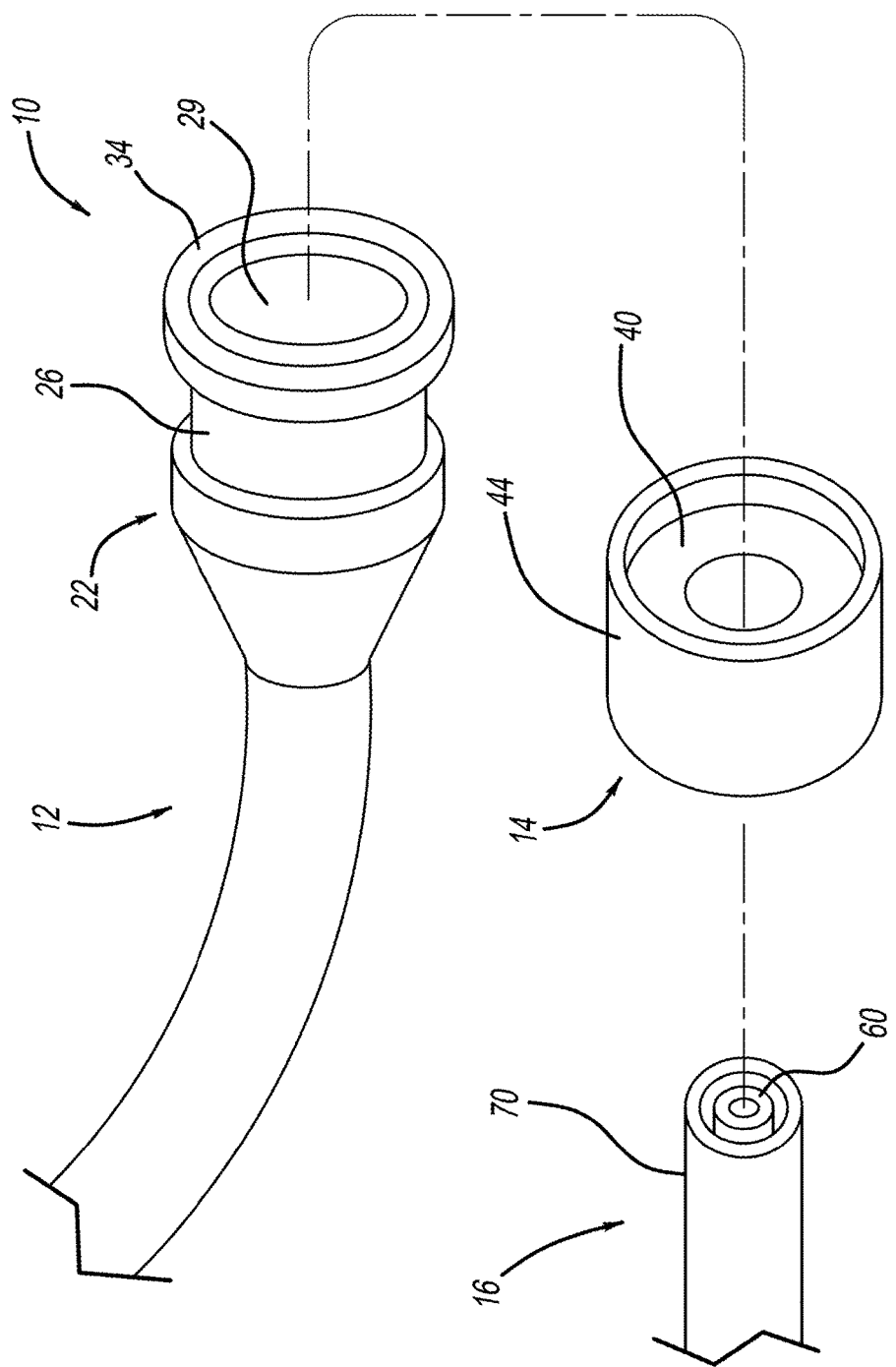
FIG. 1 is an exploded view showing an endoscope having an end and an internal magnet coupled thereto, an external ring having an external magnet and a jacket, and tubular medical device housed within an overtube.

Turning now to the figures, FIGS. 1-13 illustrates a system 10 including an endoscope 12, an external ring 14, and a tubular medical device 16 for creating an external percutaneous fluidic connection. More specifically, FIG. 1 shows an endoscope 12 having an end cap 22 defining a distal cavity 29 and an internal magnet 34 at its distal end. The endoscope 12 and internal magnet 34 are configured for being inserted and disposed within a body cavity. FIG. 1 also shows the external ring 14 having an external magnet 40 which is configured to be placed externally on the skin to mate with the internal magnet 34 disposed within the body cavity. After an incision is created through the magnets 34 and 40, the tubular medical device 16 is configured to be inserted through the magnets 34 and 40 and into the end cap 22. This provides for a fast and reliable method of placing the tubular medical device 16 in a patient without the need for guidewires, pull wires, snares, or delivery of the tubular medical device 16 through the upper GI tract. The mating of the internal magnet 34 and external magnet 40 presses the body cavity wall against the patient's skin, and the incision through the body cavity wall and skin can be performed simultaneously, with the cutting tool extending into the distal cavity 29.

Generally, the device 16 is depicted as a gastrostomy feeding device (e.g., a PEG tube), however it will be recognized by those skilled in the art that the device 16 can be applied to form many different external percutaneous connections, including IV lines, internally placed catheters, dialysis lines, colostomy bags and the like. Various known PEG devices can be used as the device 16, which will be described in further detail below.

The endoscope 12 can resemble a typical endoscope or other elongate medical device capable of being inserted into a patient's gastrointestinal tract and toward and into the stomach or other internal bodily organ. While the term "endoscope" is generally used throughout the description, it will be appreciated that the term can refer to these other elongate medical devices, such as other catheter based fiberoptics or devices that can be inserted through natural or artificial orifices and fed through a body passage toward a target location within the body.

One type of endoscopic device capable of use is the Olympus GIF-160, which includes a light, imaging device (e.g. a camera, lens, or the like), water channel, and access channel. The outer diameter of the endoscopic device is approximately 0.59 inches. However, it will be appreciated that various other known endoscopic devices, such as other traditional esophageal diagnostic scopes or "upper" endoscopes, could also be used to fit the desire of the particular user. While the system 10 can be used in various internal organs, reference to the stomach and abdomen will be primarily described.

With reference to FIG. 2A, the endoscope 12 has a proximal end 18 and a distal end 20. The proximal end 18 can include a handle (not shown) or other mechanism for manipulating the endoscope 12 through a patient's body and into a desired position within the body. The endoscope 12 is generally flexible while retaining sufficient rigidity to allow it to be pushed through a patient's body toward the target site. The type of endoscope 12 can be a traditional endoscope sized and configured to extend through a patient's mouth, the upper GI tract, and out through a hole in the patient's abdomen. The length of the endoscope 12 can be approximately 160 cm; however, other lengths could also be used that are long enough to extend out of the mouth, through the upper GI tract, and through the patient's abdomen. Thus, it will appreciated that various lengths could apply to patient's having various body sizes.

The distal end 20 of the endoscope 12 can include the end cap 22 with a tapered barrel 24 having a frustoconical shape that tapers from a larger diameter at the distal end and a smaller diameter at the proximal end. The end cap 22 further includes a tube 26 extending distally from the barrel 24. The end cap 22 includes a proximal facing cavity 27 defined by the barrel 24. The tube 26 defines a distal facing cavity 29. A shelf 32 extends transversely between the proximal cavity 27 and the distal cavity 29. The shelf 32 will seal the distal end of the endoscope 12, and any accessory channels therein, from the distal cavity 29. The cavity 27 is sized to receive the endoscope 12 therein, and the end cap 22 can thereby be attached to the endoscope 12 via adhesive, welding, bonding, friction fit, a threaded connection, or the like. The endoscope 12 can contact the shelf 32 such that the shelf 32 acts as a stop, allowing a pushing force exerted on the endoscope 12 to be transferred to the end cap 22. The cavity 27 is generally sized to correspond to the size of the distal end 20 of the endoscope 12. In a friction fit connection, the passageway 27 is slightly smaller than the outer diameter of the endoscope 12. The barrel 24 is preferably made from a slightly flexible biocompatible polymer to aid in creating a friction fit as well as flex slightly as the endoscope 12 flexes and bends.

The shelf 32 is preferably made of a clear plastic or polymer material that is biocompatible, such as a polycarbonate material or other acrylic material. Similarly, the tube 26 is preferably made of a clear plastic or polymer material that is biocompatible, such as a polycarbonate material or other acrylic material. The clear material of the shelf 32 and tube 26 will allow for a light or imaging device of the endoscope 12 to have a clear field of view through tube 26 such that the endoscope 12 can perform traditional endoscopic functions. The shelf 32 and tube 26 are preferably made from a single unitary piece due to their similar material properties; however, the shelf 32 and tube 26 could be separately formed and attached via an adhesive, bonding, welding, or the like. The diameter of the distal cavity 29 of the tube 26 is preferably about 0.50 inches, the thickness of the tube is preferably about 0.1 inches, and the length of the tube 26 is preferably between about 1 and 2.5 inches. However, it will be appreciated that the sizing of the tube 26 can vary depending on the needs of the user or the length of the device 16, which is further described below.

As shown in FIGS. 2B and 2C, in one form, the endoscope 12 can include an accessory channel 33 extending therethrough for providing air out of the distal end of the endoscope 12 to insufflate the body cavity at a desired location. For example, air can be blown into the body cavity to assist in pushing the body cavity wall against the abdominal wall or to provide an improved field of view for the endoscope camera.

In this form, the barrel 24 can include a cutout channel 24a having a pair of openings 24b in the wall of the barrel 24, such that the openings 24b are in fluid communication with the accessory channel 33 to allow air to flow around the shelf 32 and be expelled distally toward the body cavity wall.

With reference to FIGS. 2A-3, the system 10 further includes an annular or ring-shaped internal magnet 34 attached to a distal end of the tube 26. The magnet 34 is circumferentially arranged around the distal end of the tube 26. The magnet 34 defines an aperture 36, through which the tube 26 at least partially extends.

The magnet 34 can be fixedly bonded to the tube 26 through welding, adhesives, friction fit, or other known biocompatible attachment methods. The magnet 34 is preferably in the form of a neodymium magnet or neodymium iron boron magnet. The magnet 34 can be plated to enhance the ability to clean the magnet 34 after use. The magnet 34 preferably has a Magnet Field strength (Br) ranging from 11.1 kGa to 14.7 kGa. However, it will be appreciated that other strengths of the magnets can also be used to account for different patient anatomy, further described below.

The magnet 34 has an outer diameter D1 and an inner diameter D2. The inner diameter D2 is sized to correspond to an outer diameter of the tube 26 such that the tube 26 can be received within the aperture 36 defined by the magnet 34. Thus, the inner diameter D2 generally corresponds to the diameter of the cavity 29 plus the thickness of the tube 26 or, put another way, the outer diameter of the tube 26. In one form, the inner diameter D2 can be about 0.6 inches when the diameter of the cavity 29 is 0.5 inches and the thickness of the tube 26 is about 0.1 inches. The outer diameter of the internal magnet 34 is preferably between about 0.75 inches and 1.25 inches, and the height of the internal magnet is preferably about 0.25 inches. However, it will be appreciated that these sizes are merely exemplary, and the sizing of the magnet 34 can vary depending on the needs of the user or desired strength of the magnet 34.

The magnet 34 and end cap 22 are preferably reusable. In this regard, the magnet 34 and end cap 22 can be coated with Parylene or metal plating to enhance the ability to clean the magnet 34 and end cap 22 after use.

The magnet 34 preferably defines a distal face 34a and a proximal face 34b. When the magnet 34 is attached to the tube 26, the distal end of the tube 26 preferably does not extend distally past the distal face 34a of the magnet 34. In one form, the distal end of the tube 26 is flush with the distal face 34a of the magnet 34. However, in another form, the distal end of the tube 26 is disposed proximally from the distal face 34a of the magnet 34, while remaining distal of the proximal face 34b, such that the end of the tube 26 extends at least partially into the aperture 36.

The aperture 36 of the magnet 34, along with the distally facing cavity 29, therefore allows for an instrument or other object to be received within the cavity 29 of the tube 26 while extending distally through and beyond the magnet 34.

Thus, the endoscope 12, with the end cap 22 attached to the distal end 20 of the endoscope 12, can deliver the internal magnet 34 through a patient's body and toward a target site. For example, the endoscope 12 can deliver the internal magnet 34 by being inserted through a patient's mouth and through the upper GI tract and into the stomach. With the internal magnet 34 and end cap 22 attached to the distal end 20 of the endoscope in a generally fixed manner, the endoscope 12 can be pushed against an inner wall of the stomach, which ultimately pushes the internal magnet 34 against the wall.

These primarily internal components (the endoscope 12, end cap 22, and internal magnet 34) are configured to cooperate with various external components, described below.

With reference to FIG. 4, the system 10 includes an external ring 14 that is sized and configured to fit with the end cap 22 of the endoscope 12. The external ring 14 includes the external magnet 40 having an annular or ring shape that defines an aperture 42. The magnet 40 can be coated with neodymium, or plated, and can also be a neodymium iron boron magnet. The magnet 40 preferably has a Magnet Field strength (Br) ranging from 11.1 kGa to 14.7 kGa. However, it will be appreciated that other strengths of the magnets can also be used to account for different patient anatomy. For example, the external magnet 40 mates with the internal magnet 34 with a body cavity wall and abdominal wall/skin sandwiched therebetween. The abdominal walls of patients can vary, so a stronger magnet may be necessary to account for a greater distance between the magnets 34 and 40.

The external ring 14 can also preferably include a jacket 44 circumferentially surrounding the magnet 40, where the jacket 44 has a similar annular or ring shape. The jacket 44 has an inner diameter that is sized to correspond to the outer diameter of the magnet 40. The jacket 44 is preferably made from stainless steel, but could be made from another material, such as plastic. The jacket 44 and magnet 40 are fixedly connected via known attachment techniques, such as bonding, welding, adhesives, or mechanical or friction fitting.

The external magnet 40 has a longitudinal height that is less than the longitudinal height of the jacket 44, and is attached such that the external magnet 40 is recessed within the jacket 44 to create a step, ledge, or counter-sunk type recess 45. The magnet 40 is preferably longitudinally centered within the jacket 44, such that two recesses 45 are defined on each side of the magnet 44. The external magnet 40 and jacket 44 can thereby be installed without requiring the user to orient any particular side against the patient's skin. In one form, the height of the magnet 40 is about 0.25 inches, and the height of the jacket is about 0.5 inches, such that the depth of the recess 45 is about 0.125 inches on both sides of the magnet 40. However, it will be appreciated that these sizes are exemplary and other dimensions could also be used to suit the needs of the user. For example, the magnet 40 could have a height of about 0.5 inches and the jacket 44 could have height of about 1 inch.

The external magnet 40 has an outer diameter D3 and an inner diameter D4. The inner diameter D4 preferably corresponds to the inner diameter D2 of the magnet 34, such that the inner diameters D2 and D4 will tend to align. The outer diameter D3 is preferably greater than the outer diameter D1 of the magnet 34. For example, the outer diameter D3 can be about 1 inch when the outer diameter D1 of the internal magnet 34 is about 0.75 inches.

The magnet 40 is preferably reusable. In this regard, the magnet 40 and can be coated with Parylene or metal plating to enhance the ability to clean the magnet 40 after use.

FIG. 5 illustrates the end cap 22, the internal magnet 34, the external magnet 40, and the jacket 44 in an exploded view, illustrating the relative widths in one embodiment. Of course, it will be appreciated that other relative widths of these components could also be used.

The internal magnet 34 and external magnet 40 are preferably sized so that the magnet 34 can be received within the jacket 44 when the magnet 34 is drawn toward the external magnet 40, which will be further described below. As such, it will be appreciated that further modifications of the relative diameters of the internal magnet 34 and external magnet 40 can be accomplished by a skilled artisan such that the magnet 34 can be received within the jacket 44. However, it will also be appreciated that magnet 34 can still become magnetically coupled with the external magnet 40 in cases where there is no jacket 44, or if the jacket 44 does not define a recess with the external magnet 40. Thus, for example, the external magnet 40 could have an outer diameter D3 that is smaller than the outer diameter D1 of the internal magnet 34 and the magnets 34 and 40 can still align and be sufficiently magnetically coupled.

For purposes of discussion, however, the magnets 34 and 40 will be described such that the magnet 34 can be received within the jacket 44 attached to the external magnet 40.

With reference to FIG. 6, when the magnets 34 and 40 are aligned and mated, and the magnet 34 is received within the jacket 44. The jacket 44, internal magnet 34, and external magnet 40 can combine to define an annular channel 50 extending circumferentially between the outside of the magnet 34 and the inside of the jacket 44. This channel 50 can allow for body tissue to be received when the magnets 34 and 40 are mated, further described below. The size of the annular channel 50 will depend on the size of the magnets 34 and 40 and the jacket 44. FIG. 6 shows the magnets 34 and 40 contacting each other in a contacting position. However, when deployed, the internal magnet 34 will be disposed inside the stomach, and the external magnet 40 will be disposed outside of the patient's skin. Thus, there will be a gap between the magnets 34 and 40 corresponding to the thickness of the patient's skin and the stomach wall, which will be further illustrated and described below.

With reference to FIG. 7A, the device 16 is sized and configured to be received through the apertures 36 and 42 of the magnets 34 and 40, respectively, when the magnets 34 and 40 are aligned. More specifically, the device 16 includes a first tube 60 which is placed through an opening in the abdominal wall and corresponding opening in the stomach wall (i.e. a stoma). A proximal end 62 of the tube 60 remains accessible from outside of the body, while a distal portion 64 of the tube 60 is positioned inside of the stomach. The first tube 60 is supported by a first anchor 66 that is positioned along an interior surface of the stomach (FIG. 13), and a second anchor 67 (FIG. 13) that is positioned along an exterior of the abdomen.

The proximal end 62 of the tube 60 remains accessible to the patient and medical professional, for example for the introduction of food or medication. Accordingly, the proximal end 62 is adapted for connection to a feeding pump, syringe or the like.

In one form, the first anchor 66 of the first tube 60 is in the form of an expandable member 68 located adjacent the distal end 34 of the first tube 60. The expandable member 68 is preferably an inflatable balloon, although those skilled in the art will recognize that the anchor 66 may comprise many structures including expandable wings, correctional threads and the like. The second anchor 67 can be in the form of various known external anchors, such as an expandable member, expandable wings, correctional threads, a slidable flange, and the like.

The device 16 has a compressed delivery configuration and an expanded deployed configuration. As shown in FIG. 7A, the device 16 can include an overtube 70 that receives the tube 60 in the delivery configuration. The overtube 70 has a generally tubular shape having a proximal opening 72, a distal opening 74, and a lumen 75 extending therebetween. The overtube 70 has an outer diameter that is less than or equal to the inner diameters of magnets 34 and 40 and the inner diameter of the tube 26. Thus, the overtube 70, having the device 16 in the delivery configuration therein, can extend through the magnets 34 and 40 and into the cavity 29 defined by the tube 26, so that the overtube 70 extends from outside to inside the body.

The device 16 further includes a deployed configuration (FIG. 13), where the overtube 70 is removed, and the anchor 66 or expandable member 68 is allowed to expand inside the stomach to anchor the device 16 and retain the distal end 64 therein. While the device 16 has been described as including the overtube 70, it will be appreciated that the device 16 could be used without the overtube 70.

With reference to FIG. 7B, in an alternative embodiment, a device 116 can include a tube 60 that is housed within an overtube 170. The overtube 170 can include an upper portion 172 and a lower portion 174. The upper portion 172 can include a reduced diameter connection portion 176. The connection portion 176 is sized to be received within a connection cavity 178 defined by the lower portion 174.

The lower portion 174 can have a generally tapered shape defining a distal tip 180, where the outer diameter of the lower portion 174 becomes smaller at distances further from the upper portion 172. The cavity 178 is at the end of the lower portion 174 opposite the distal tip 180.

The upper and lower portions 172, 174 are sized to cooperate to form the overtube 170, where the connection portion 176 is received within the cavity 178 in a friction fit or other connection that can be manually decoupled. In another form, the upper and lower portions 172, 174 can be connected via a threaded connection.

With reference to FIG. 7C, the overtube 170 can further include a locking channel 182 formed on the exterior of the body of the lower portion 174. The locking channel 182 can have various shapes, such as a "T" shape or an "L" shape. The locking channel 182 extends between a cylindrical portion 184 and a tapered portion 186 of the lower portion 174, such that the locking channel 182 blends into the tapered portion 186 to create an entry point 188. The locking channel can have a width of about 1/16 inch.

In this embodiment, a tube 126 of the end cap 22 can include an inwardly projecting peg 190 extending into a cavity 129 defined by the tube 126. The peg 190 is sized to be received within the locking channel 182 and to slide longitudinally within the locking channel 182 when the overtube 170 is inserted into the cavity 129. The overtube 170 can be twisted such that the peg 190 will slide laterally within the locking channel 182 after sliding longitudinally. With the overtube 170 locked in place, the upper portion 172 can be de-coupled from the lower portion 174, leaving the lower portion 174 locked in place within the cavity 129.

In another form, as shown in FIGS. 7E and 7F, the channel 182 can have a decreasing width to create a friction fit in response to translation relative to the peg 190. For example, as the overtube 170 is translated into the cavity 129, the peg 190 will slide within the channel 182. As the width decreases, the friction between the peg 190 and the channel 182 will increase, thereby creating a friction fit. In this approach, the channel 182 can be generally straight and aligned longitudinally as shown in FIG. 7F. However, it will be appreciated that this approach could also be used in the other shapes of the channel 182 described herein, such as the "T" shaped channel 182 shown in FIG. 7E.

In another approach, similar to the decreasing width of the channel 182, the depth of the channel 182 can decrease to increase the strength of the friction fit in response to continued translation of the overtube 170, as shown in FIG. 7G. In yet another approach, both the width and depth of the channel 182 can decrease.

Having described the general structure of the system 10 and its components the use of the system 10 will now be described. The system 10 can be advantageously used in percutaneous endoscopic gastronomy procedures without the need for delivering the device 16 through the upper GI tract.

With reference to FIG. 8, the endoscope 12 having the end cap 22 and magnet 34 is inserted into a orifice of the body. Preferably, the endoscope 12 is inserted through the patient's mouth or other natural orifice; however, the endoscope 12 could also be delivered to a non-natural orifice, such as via an incision. The endoscope 12 is delivered through the patient's upper GI tract and toward and into the patient's stomach. However, it will be appreciated that the endoscope 12 could be delivered through other body passageways and/or to other body cavities.

Once the endoscope 12 is inside the stomach, the user can illuminate a light or illuminating device of the endoscope 12, and force the end cap 22 of the endoscope 12 against an inner surface of the stomach wall. By pushing on the stomach wall from inside, the stomach will be pushed toward the abdomen, and the space between the stomach and the abdomen will be reduced or eliminated, with fluids or other organs being pushed aside. With the end cap 22 pressed against the stomach wall, the internal magnet 34 is also pressed against the stomach wall.

In addition to the pushing forces, the area adjacent the distal end of the endoscope 12 can be insufflated by the endoscope 12, which can help force the stomach wall away from the endoscope 12 and toward the abdominal wall. This optional insufflation can be used in addition to the pushing force. However, it will be appreciated that the pushing force can be used without the insufflation.

With the end cap 22 pressed against the stomach wall, the light or other illuminating device of the endoscope can be illuminated to assist in determining the location of the magnet 34 from outside the patient. For example, a portion of the patient's abdomen may become brighter to indicate the location of the endoscope 12 being pressed against the stomach. The user may also notice a bulge at the location of the endoscope 12.

With reference to FIG. 9, once the internal magnet 34 is pressed against the stomach wall and the location is identified from outside the body, the external magnet 40 with the jacket 44 is placed on an external surface of the body corresponding to the location of the internal magnet 34 disposed inside the body. The magnet forces of the magnets 34 and 40 will cause them to be drawn together into a magnetic mating connection. The stomach and skin will be sandwiched between the magnets 34 and 40. The annular channel 50 will allow the stomach wall and skin to be partially received therein. The strength of the magnetic connection will keep the magnets 34 and 40 together. More specifically, the shape of the magnets 34 and 40, and their generally corresponding inner diameters will cause the magnets 34 and 40 to be generally coaxially aligned. This coaxially alignment urged by the magnets 34 and 40, as well as the shape of the jacket 44, will keep the magnets 34 and 40 in an aligned configuration.

With reference to FIG. 10, with the magnets 34 and 40 aligned, the user can create an incision through aperture 42 of the external magnet 40 as well as through the aperture 36 of the internal magnet 34. The incision thereby creates a stoma 80 through the skin and stomach wall, allowing access into the cavity 29 defined by the tube 26. The size of the incision is smaller than the inner diameters of the magnets 34 and 40. Preferably, the size of the incision is slightly smaller than the diameter of the tube 60 of the device 16, so that when the tube 60 is left in place at the completion of the procedure (further described below), there will be a generally tight fit between the tube 60 and the stoma 80 to limit leakage therebetween. It will be appreciated that the creation of the stoma 80 by way of incision is one example, and other known methods and devices for providing access through layers of body tissue can also be used. For example, a common trocar can be used to create the incision, or a scalpel or other cutting instrument could be used.

After creating the stoma 80, the cavity 29 is thereby accessible from outside the body. The mated configuration of the magnets 34 and 40 also preferably creates a generally fluidic seal between the magnet 34 and the stomach wall, thereby limiting fluid communication between the interior of the stomach and the cavity 29 when the magnets 34 and 40 are mated. Thus, the user can penetrate past the skin and past the stomach wall while limiting exposure of the stomach contents to the exterior of the body during the procedure.

With reference to FIG. 11A, after the stoma 80 has been created by the incision, the device 16, including the overtube 70 and tube 60, can be inserted into the cavity 29 from outside the body through the stoma 80. The distal end 64 of the first tube 60 is inserted into the cavity 29 so that the anchor 66 is disposed within the cavity 29 and past the stomach wall. At this point, the first tube 60 and the overtube 70 extends between the exterior of the body and the interior of the stomach.

In an alternative approach, and with reference back to FIG. 7B, the device 116 including the overtube 170 and tube 60 is inserted into the cavity 129 having the peg 190. FIG. 7B shows the relationship between the device 116 after being inserted into the cavity 129 of the tube 126, while omitting the layers of skin and external magnet 40, and other components shown in FIGS. 10 and 11 for clarity. The overtube 170 is aligned such that the channel 182 is in line with the peg 190. The tapered shape of the lower portion 174 of the overtube 170 will cause the stoma 80 (FIG. 10) to stretch or dilate as the overtube 170 is inserted therethrough. As the overtube 170 is inserted into the cavity, the peg 190 will be received in the channel 182. The lower portion 174 is then locked in position relative to the cavity 129, depending on the size and shape of the channel 182. For example, when the channel has a "T" or "L" shape, the overtube 170 can be rotated after insertion. In the case of a reduced width or depth of the channel 182, the overtube 170 may become locked by insertion only, or by insertion and rotation. It will be appreciated that other manners of locking the lower portion 174 with the use of a peg and channel can also be used.

With reference to FIG. 11B, upon locking the overtube 170 relative to the cavity 129, the upper portion 172 of the overtube 170 can be decoupled from the lower portion 174. In one approach, the friction fit between the upper and lower portions 172, 174 can be overcome by pulling or twisting or other methods of de-coupling a tubular friction fit. In the case of a threaded connection, the upper and lower portions 172, 174 can be decoupled by rotation in a manner known in the art. It will be appreciated that other mechanical connections, such as a snap fit or the like, can be similarly de-coupled in a manner known in the art.

After de-coupling, the lower portion 174 remains coupled within the cavity 129, and the upper portion 172 remains extending through the stoma 80. It will be appreciated, however, that the upper portion 172 may be retracted such that it is disposed outside of the stoma 80 on the exterior side due to the de-coupling step.

As shown in FIG. 11B, the anchor 66 is disposed beyond the distal end of the tube 60. However, it will be appreciated that the anchor 66 could be positioned within the upper portion 172 after decoupling, such that it is still distally beyond the stoma 80. The anchor 66 can be expanded upon retraction of the tube 126 and lower portion 174 such that the anchor 66 is exposed, as further described below. In the event the anchor is disposed within the upper portion 172, it can be expanded after being exposed from the upper portion 172, as further described below.

Figure 12:
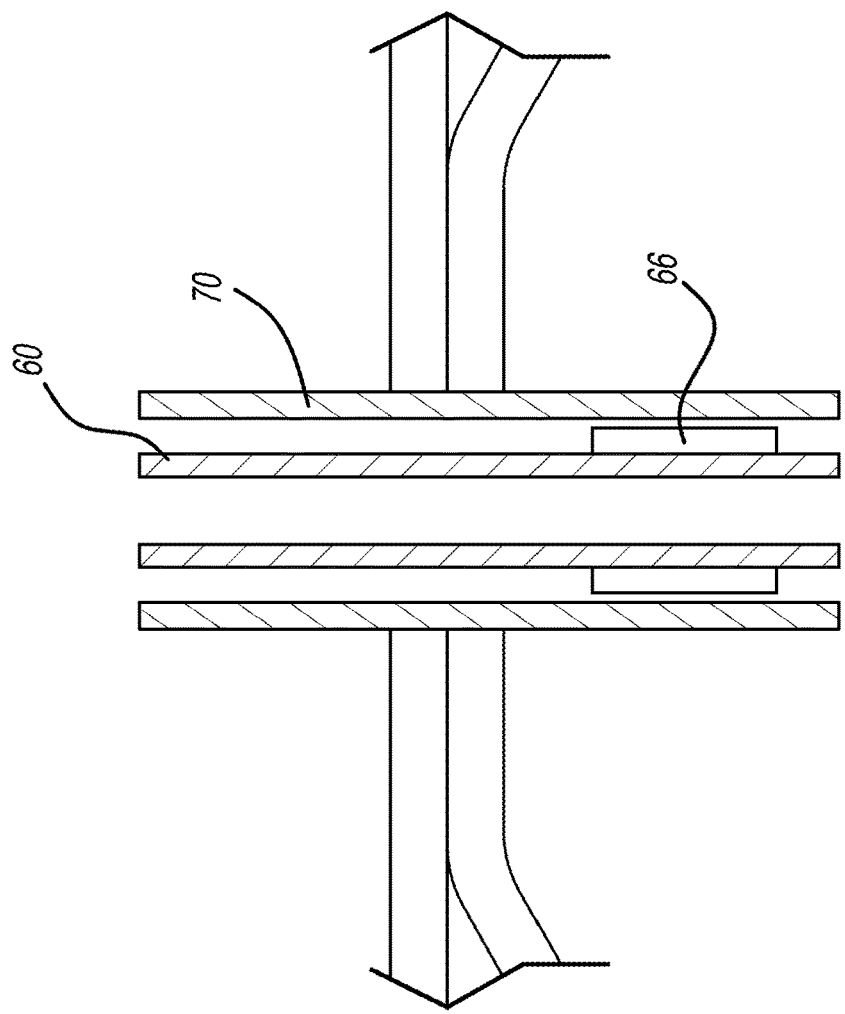
FIG. 12 is a schematic view showing the inner and external magnets decoupled and the overtube remaining extending through the incision.

The following description regarding decoupling of the magnets 34, 40 and removal of the overtube 70 can apply to the upper portion 172 as well, as the upper portion 172 remains extending through the skin and into the body cavity, similar to the overtube 70 shown in FIG. 12.

With reference to FIG. 12, once the overtube 70 containing the tube 60 is in place and extending through the skin and the stomach wall, the external magnet 40 and jacket 44 can be decoupled from the internal magnet 34 attached to the end cap 22. The external magnet 40 and jacket 44 can be retracted along the overtube 70 and set aside. With the internal magnet 34 decoupled from the external magnet 40, the endoscope 12, having the end cap 22 and internal magnet 34 coupled thereto, can be retracted from the stomach wall and retracted from the body through the upper GI tract and out of the mouth or other initial entry point. With the external magnet 40 and endoscope 12 removed, the overtube 70 having the tube 60 contained therein remains in place extending from outside the body and into the stomach. The anchor 66 of the tube 60 remains disposed within the stomach. In the case of upper portion 172, the upper portion 172 may extend through the stoma 80 at this point, or it may have been retracted from the stoma 80 previously, leaving the tube 60 in place.

In another approach, the magnets 34 and 40 can be decoupled in response to retracting the endoscope 12. Retraction of the endoscope 12 will cause the internal magnet 34 coupled thereto to be pulled away from the external magnet 40, thereby de-coupling the magnetic connection. As such, de-coupling of the magnets 34, 40 does not have to occur prior to beginning the retraction of the endoscope 12.

Figure 13:
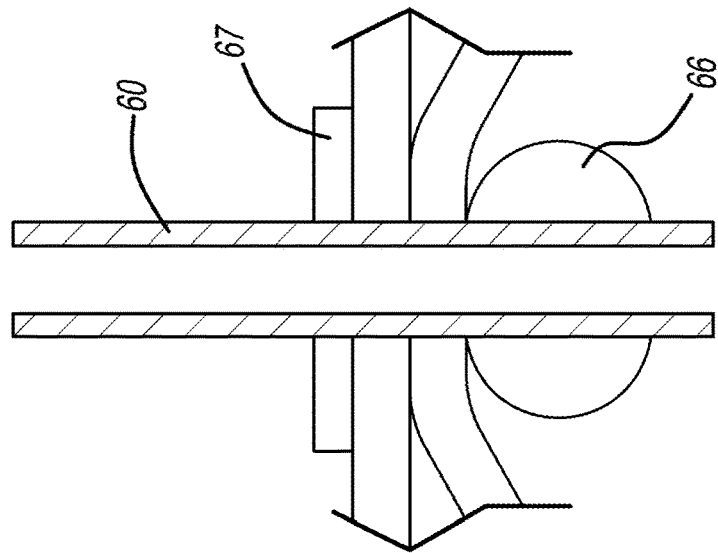
FIG. 13 is a schematic view showing the tubular medical device anchored and extending through the patient's skin and body cavity wall.

With reference to FIG. 13, the overtube 70 or upper portion 172 is retracted relative to the tube 60 such that the tube 60 remains in place and extending from outside the body and into the stomach. The anchor 66 is then expanded or otherwise deployed, thereby preventing the tube 60 from being pulled out of the stomach. The anchor 67 is then placed over the tube 60 on the outside of the body to sandwich the skin and stomach wall between the anchors 66 and 67. The tube 60 is thereby secured and in position for being attached to a food supply or the like in a manner known in the art. The anchor 66 can be a self-expanding anchor, described previously above. In this approach, the anchor 66 will generally expand automatically upon being exposed from either the overtube 70 or 170, as well as the cavity 29 or 129, such that there are no components surrounding the anchor 66 to prevent it from expanding.

It will be recognized by those skilled in the art that, while the methods described above generally include inserting the endoscope 12 through a body lumen and placing the device 16 through layers of body tissue, it will be recognized that the systems, devices and methods described herein may be used on any passageway or layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise creating holes or perforations in layers of material that are not bodily tissue. Some examples include plumbing, drainage, and related manufacturing, working with synthetic tissues, connecting or repairing polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for creating a percutaneous external connection, the medical system comprising:
   an end cap configured for being attached to a distal end of an endoscope, the end cap including a barrel and a tube, the tube defining a cavity having a distal opening facing distally and the barrel defining a proximal cavity facing proximally, and the end cap further includes a transverse shelf extending between the proximal cavity and the distal cavity that seals the proximal cavity from the distal cavity, the transverse shelf extending across the end cap and completely closing a proximal end of the distal cavity;
   an internal magnet attached to a distal end of the tube, the internal magnet being circumferentially arranged around the distal end of the tube, wherein the tube extends at least partially into an aperture defined by the internal magnet; and
   an external magnet configured for mating with the internal magnet, wherein the external magnet defines an aperture, wherein the external magnet is attracted to the internal magnet;
   wherein the apertures of the external magnet and the internal magnet are sized to define a passageway from the aperture of the external magnet into the cavity of the tube such that a further medical device may be inserted through the aperture of the external magnet and into the distal cavity of the tube.

2. The system of claim 1, further comprising a jacket attached circumferentially around the external magnet, wherein the jacket has a height greater than a height of the external magnet, wherein the jacket defines a recess therein sized to receive the internal magnet, wherein the internal magnet surrounds a radially outermost surface of the tube.

3. A medical system for creating a percutaneous external connection, the medical system comprising:

an end cap configured for being attached to a distal end of an endoscope, the end cap including a barrel and a tube, the tube defining a cavity having a distal opening and a proximal end opposite the distal opening;

an internal magnet attached to a distal end of the tube, the internal magnet being circumferentially arranged around the distal end of the tube, wherein the tube extends at least partially into an aperture defined by the internal magnet; and an external magnet configured for mating with the internal magnet, wherein the external magnet defines an aperture, wherein the external magnet is attracted to the internal magnet;

wherein the cavity of the tube and the apertures of the external magnet and the internal magnet are sized to permit passage of a tubular medical device through the apertures and into the cavity of the tube to be received therein;

wherein the end cap includes a transverse shelf adjacent the cavity of the tube for being disposed against a distal end of an endoscope to seal the distal end of the endoscope, wherein the shelf extends across the end cap and completely closes the proximal end of the cavity.

4. The system of claim 1, wherein the system includes a tubular medical device housed within an overtube, the tubular medical device has a delivery configuration and a deployed configuration, the medical device is disposed within the overtube in the delivery configuration, and the overtube is retracted in the deployed configuration.

5. The system of claim 4, wherein the tubular medical device includes an anchor disposed at an internal end thereof.

6. The system of claim 4, wherein the overtube includes an upper portion and lower portion removably coupled together, and the lower portion includes a tapered portion, wherein the lower portion includes a locking channel disposed on an outer surface thereof, and wherein the tube of the end cap includes a peg extending into the cavity of the tube, and the peg is sized to be received in the locking channel to retain the lower portion of the overtube within the cavity.

7. The medical system of claim 1 further comprising an elongate endoscope having a distal end, wherein the end cap is attached to the distal end of the endoscope, and the distal end of the endoscope is received within the proximal cavity of the barrel and is disposed against the transverse shelf.

* * * * *